United States Patent
Venkatesh

(10) Patent No.: US 8,962,022 B2
(45) Date of Patent: Feb. 24, 2015

(54) PHARMACEUTICAL COMPOSITIONS COMPRISING AN ACTIVE SUBSTANCE FROM THE SUBSTITUTED BENZHYDRYLPIPERAZINE FAMILY

(75) Inventor: Gopi Venkatesh, Vandalia, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 840 days.

(21) Appl. No.: 12/057,177

(22) Filed: Mar. 27, 2008

(65) Prior Publication Data

US 2008/0241237 A1    Oct. 2, 2008

Related U.S. Application Data

(60) Provisional application No. 60/920,224, filed on Mar. 27, 2007.

(51) Int. Cl.
| | |
|---|---|
| *A61K 9/20* | (2006.01) |
| *A61K 9/26* | (2006.01) |
| *A61K 9/24* | (2006.01) |
| *A61K 31/497* | (2006.01) |
| *C07D 295/00* | (2006.01) |
| *A61K 9/00* | (2006.01) |
| *A61K 9/50* | (2006.01) |

(52) U.S. Cl.
CPC .............. *A61K 9/0056* (2013.01); *A61K 9/2077* (2013.01); *A61K 9/5026* (2013.01); *A61K 9/5047* (2013.01); *A61K 9/5078* (2013.01)
USPC ........... 424/470; 424/464; 424/465; 424/469; 424/471; 514/252.12; 544/358

(58) Field of Classification Search
None
See application file for complete search history.

(56) References Cited

U.S. PATENT DOCUMENTS

| | | | |
|---|---|---|---|
| 7,014,867 B2 * | 3/2006 | Fanara et al. ................. | 424/472 |
| 7,226,614 B2 * | 6/2007 | Fanara et al. ................. | 424/472 |
| 2004/0170690 A1 * | 9/2004 | Fanara et al. ................. | 424/472 |
| 2004/0185099 A1 * | 9/2004 | Stark et al. .................... | 424/471 |
| 2006/0034928 A1 * | 2/2006 | Fanara et al. ................. | 424/472 |
| 2006/0057207 A1 | 3/2006 | Ziegler et al. | |
| 2006/0083786 A1 * | 4/2006 | Chaudhari et al. ............ | 424/470 |
| 2006/0105038 A1 * | 5/2006 | Lai et al. ....................... | 424/470 |
| 2006/0127479 A1 | 6/2006 | Kumaraperumal et al. | |

OTHER PUBLICATIONS

"International Preliminary Report on Patentability" from PCT/US2008/058470, 9 pages (mailed Oct. 8, 2009).
International Search Report based on International Application No. PCT/US08/58470 (Jun. 30, 2008).

* cited by examiner

*Primary Examiner* — Jeffrey T Palenik
(74) *Attorney, Agent, or Firm* — Cooley LLP

(57) ABSTRACT

The present invention is directed to compositions of taste-masked microparticles comprising a substituted benzhydrylpiperazine coated and a taste-masking layer comprising a water-insoluble polymer and a gastrosoluble polymer, and methods of making such taste-masked microparticles. The present invention is also directed to stable orally disintegrating compositions comprising taste-masked microparticles of a substituted benzhydrylpiperazine and rapidly dispersing granules, and methods of making such orally disintegrating compositions.

67 Claims, 3 Drawing Sheets

PHARMACEUTICAL COMPOSITIONS COMPRISING AN ACTIVE SUBSTANCE FROM THE SUBSTITUTED BENZHYDRYLPIPERAZINE FAMILY

CROSS-REFERENCE TO RELATED APPLICATIONS

This application claims priority to U.S. Provisional Application Ser. No. 60/920,224, entitled "Pharmaceutical Compositions Comprising an Active Substance from the Substituted Benzhydrylpiperazine Family," filed Mar. 27, 2007. The content of this provisional application is herein incorporated by reference in its entirety for all purposes.

TECHNICAL FIELD

The present application is directed to pharmaceutical compositions comprising substituted benzhydrylpiperazines such as cetirizine dihydrochloride and rapidly dissolving microgranules in the same tablet matrix (e.g., as orally disintegrating tablets), as well as methods of making and using such compositions.

BACKGROUND OF THE INVENTION

There are two types of widely used dosage forms for oral administration: tablets and capsules. However, such dosage forms have several disadvantages. For example, it is estimated that 50% of the population have problems swallowing tablets (see Seager in Journal of Pharmacy and Pharmacology, 50, pages 375-382, 1998). It is especially hard for aged persons to swallow tablets or capsules, or to medicate children who are unable or unwilling to swallow tablets or capsules. This leads to poor compliance, or even non-compliance with the treatment, and thus has a negative impact on the efficacy of the treatment.

In addition, many therapeutic agents are bitter. The bitter taste precludes the medication from being easily sprinkled onto foods such as applesauce, a commonly used method of administering medications to children. Conventional capsules or tablets are also inconvenient for patients who do not have ready access to drinking water or fluids.

Chewable tablets comprising taste-masked particles capable of being chewed without providing a bitter taste are known. However, a taste-masking coating which prevents release of a bitter-tasting drug in the oral cavity during chewing can also undesirably reduce the rate of drug release in the gastrointestinal tract. Furthermore, because of the rate reduction, the taste-masked drug product may no longer be bioequivalent to the reference listed immediate-release (IR) product.

Orally disintegrating tablet (ODT) dosage forms are also known, which rapidly dissolve or disintegrate in the oral cavity and hence can be taken without water. Ideally, an orally disintegrating tablet (ODT) formulation should rapidly disintegrate on contact with saliva in the oral cavity of the patient, should form a smooth, easy-to-swallow suspension containing taste-masked drug particles, provide a smooth mouthfeel leaving little or no aftertaste (i.e., little or minimal drug release with a non-gritty or non-chalky taste) until swallowed, and should provide rapid, substantially complete release upon arrival in the stomach. If conventional immediate-release tablet or capsule dosage forms are already approved, ODT dosage forms should also release the drug in a manner bioequivalent to the immediate-release drug product. However, it can be quite difficult to formulate ODT compositions which disintegrate rapidly with good organoleptic properties (e.g., little or no bitter taste) and still release the drug rapidly within the gastrointestinal tract.

Undesirable taste is one of several important formulation problems that are encountered in providing patient-friendly dosage forms such as oral disintegrating tablets. These patient-friendly dosage forms could significantly improve convenience and efficacy by enhancing compliance with the dosing regimen. The techniques most often employed for achieving effective taste-masking include various physical and chemical methods such as use of combinations of flavors and sweeteners, polymer coating, inclusion complex formation with cyclodextrins, mixing/treating with ion exchange resins, solubility limiting methods, liposomes, microemulsions and numbing of taste buds.

Much effort has been devoted to developing coating processes such as aqueous and non-aqueous coacervation, fluid-bed coating, etc., for coating bitter drug particles with polymers that are water-soluble, water-insoluble or soluble under alkaline pH conditions. The type and amount of coating applied depends on the physicochemical properties of the drug, especially its particle size, shape, aspect ratio, particle size distribution, solubility in neutral to saliva pH liquids, organoleptic properties (i.e., extent of bitterness), dose, and the dosage form application (e.g., chewable or ODT).

An undesirable consequence of taste-masking using a water-insoluble polymer is the generally slower release of the drug in the gastrointestinal tract. One approach for addressing this problem is described in U.S. patent application Ser. No. 11/213,266 filed Aug. 26, 2005 (U.S. Pub. No. 2006/0105038), the contents of which are hereby incorporated by reference. The '266 application discloses substituted benzhydrylpiperizines granulated in the presence of cellulose and cellulose derivatives, taste-masked by microencapsulation (coacervation) with a water-insoluble polymer in combination with a gastrosoluble organic or inorganic pore-former.

Cetirizine ($C_{21}H_{25}ClN_2O_3$), represented chemically as 2-[2-{4-[(4-chlorophenyl)phenylmethyl]-1-piperazinyl}ethoxy]acetic acid, belongs to a class of drugs known as substituted benzhydrylpiperazines which are reported to exhibit a bitter taste, as disclosed in EP 0 811 374. Cetirizine and its dihydrochloride salt are well known for their antihistamine properties. Cetirizine dihydrochloride is freely soluble in gastrointestinal fluids. Its high solubility together with its extremely bitter taste often results in poor compliance of the regimen. Chewable tablets have been developed for oral administration, especially for administering to children. However, cetirizine dihydrochloride taste-masked by complexation in cyclodextrin and conventional chewable tablet ingredients such as mannitol or sorbitol were required, from stability considerations, to be confined into two separate layers of a bi-layer tablet. By so doing, intimate contact between mannitol, the primary ingredient of the group of polyols widely used in conventional chewable tablets, and cetirizine, which is highly susceptible to degradation in the presence of polyols, is minimized. Substituted benzhydrylpiperazines, including cetirizine dihydrochloride, have been reported to interact with certain polyols including mannitol resulting in undesired reaction products. These reaction products are reported to increase in the presence of water and/or higher temperature.

EP 0 811 374 recommends not to use any of the polyols, especially those with a molecular weight of less than 900, particularly less than 300, in the dosage form and/or to coat the active with cellulosic or methamethacrylate polymers. The dosage form described therein as a preferred embodiment demonstrates the absence of palatability improving polyols, excepting a high molecular weight polyethylene glycol.

Chewable tablet formulations comprising cetirizine and palatable polyols have been described wherein these two components are present in two separate layers of a bi-layer tablet. Because of the instability of such formulations (presumably caused by the interaction of cetirizine and polyols), so far no orally disintegrating tablet (ODT) formulations of cetirizine are available even though ODT formulations have been developed and marketed for antihistamines of other chemical classes, such as loratidine. Thus there still exists an unmet need for substituted benzhydrylpiperazine-containing ODT compositions with improved long-term storage stability, and which provide plasma concentration profiles bioequivalent to existing conventional non-ODT dosage forms, while maintaining effective taste-masking properties and acceptable mouthfeel.

SUMMARY OF THE INVENTION

In one embodiment, the present invention is directed to a composition comprising taste-masked microparticles each comprising (a) a core particle comprising a substituted benzhydrylpiperazine or a pharmaceutically acceptable salt, ester, and/or solvate thereof, and (b) a taste-masking layer comprising a water-insoluble polymer and a gastrosoluble polymer. The taste-masking layer substantially masks the taste of the substituted benzhydrylpiperazine and/or the pharmaceutically acceptable salt, ester, or solvate thereof.

In another embodiment, the present invention is directed to an orally disintegrating composition comprising microparticles comprising (a) a core particle comprising a therapeutically effective amount of a substituted benzhydrylpiperazine or a pharmaceutically acceptable salt, ester, and/or solvate thereof and (b) a taste-masking layer comprising a water-insoluble polymer and a gastrosoluble polymer. The taste-masking layer substantially masks the taste of the substituted benzhydrylpiperazine or pharmaceutically acceptable salt, ester, and/or solvate thereof. After administration to a patient in need thereof, the taste-masked composition substantially disintegrates in the oral cavity of the patient.

In another embodiment, the present invention is directed to an orally disintegrating composition comprising (a) taste-masked microparticles comprising a therapeutically effective amount of cetirizine or a pharmaceutically acceptable salt, ester, and/or solvate thereof; and (b) rapidly dispersing granules comprising (i) a disintegrant and (ii) a sugar alcohol, a saccharide, or a mixture thereof.

In another embodiment, the present invention is directed to a method of treating or preventing an allergic or inflammatory disorder comprising administering to a patient in need thereof a composition comprising microparticles comprising: (a) a core particle comprising a substituted benzhydrylpiperazine or a pharmaceutically acceptable salt, ester, and/or solvate thereof; and (b) a taste-masking layer comprising a water-insoluble polymer and a gastrosoluble polymer, wherein said taste-masking layer substantially masks the taste of the substituted benzhydrylpiperazine or pharmaceutically acceptable salt, ester, and/or solvate thereof.

In another embodiment, the present invention is directed to a method of preparing a composition comprising taste-masked microparticles comprising (a) preparing core particles comprising a substituted benzhydrylpiperazine or a pharmaceutically acceptable salt, ester, and/or solvate thereof; and (b) layering said core particles with a taste-masking layer comprising a water-insoluble polymer and a gastrosoluble polymer, wherein said taste-masking layer substantially masks the taste of the substituted benzhydrylpiperazine or pharmaceutically acceptable salt, ester, and/or solvate thereof.

In another embodiment, the present invention is directed to a method of preparing an orally disintegrating composition comprising (a) coating core particles comprising a substituted benzhydrylpiperazine or a pharmaceutically acceptable salt, ester, and/or solvate thereof with one or more taste-masking layers to form coated microparticles; (b) preparing granules comprising (i) a disintegrant and (ii) a sugar alcohol, a saccharide, or a mixture thereof; (c) mixing said coated microparticles and said granules to form a compressible blend; and (d) compressing said compressible blend into tablets.

DETAILED DESCRIPTION OF THE INVENTION

Figure 1:
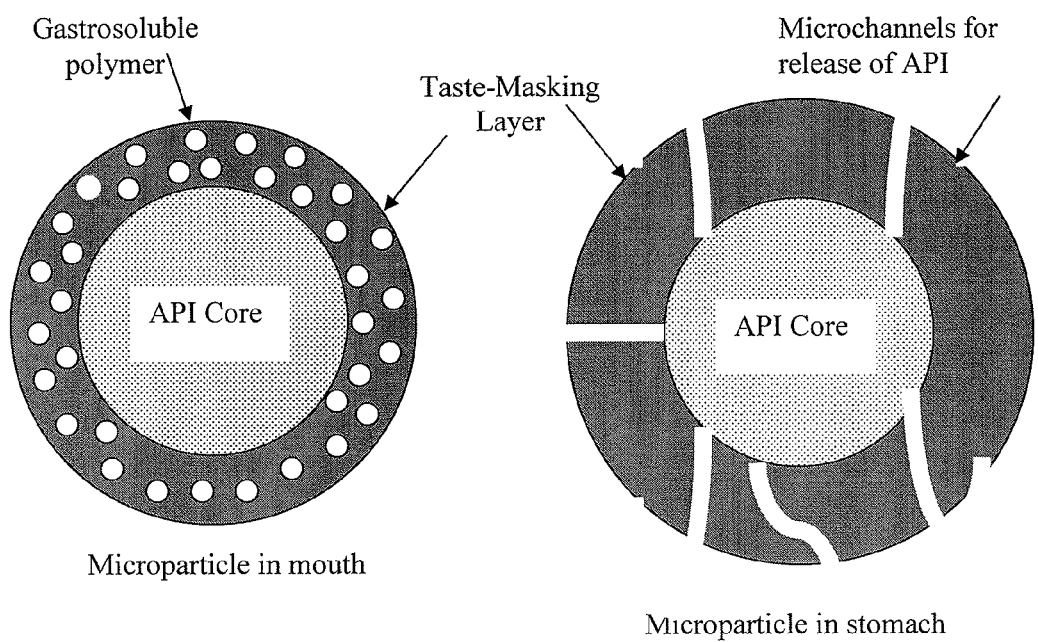
FIG. 1 shows an embodiment of a structure of a drug core taste-masked with a water-insoluble polymer in combination with a gastrosoluble polymer in the mouth (left) and in the stomach (right).

All documents cited are incorporated herein by reference for all purposes; the citation of any document is not to be construed as an admission that it is prior art with respect to the present invention.

The terms "drug", "active", "active ingredient" or "active pharmaceutical ingredient", or "API" as used herein are equivalent and include the base drug, active, active pharmaceutical ingredient, or API, as well as any pharmaceutically acceptable salt, ester, and/or solvate thereof, and mixtures thereof. These terms also include, when present, an stereoisomer or mixture of stereoisomers, including enantiomers, diastereomers, racemic mixtures, or combinations thereof. These terms represent any therapeutic agent indicated for oral administration. More particularly, the term represents any therapeutic agent indicated for oral administration belonging to a class of drugs known as substituted benzhydrylpiperazine, for example those which have a bitter taste. Examples include, but are not limited to hydroxyzine, cetirizine, efletirizine, meclizine, and buclizine, the optically active isomers thereof and the pharmaceutically acceptable salts, esters, and/or solvates thereof. In one embodiment, the substituted benzhydrylpiperazine is cetirizine, in other embodiments levocetirizine dihydrochloride. Although the description herein refers primarily to cetirizine, the present invention is not to be construed as being limited thereto.

The term "core particle" as used herein includes a particle containing an active pharmaceutical ingredient or drug. It is used interchangeably with "API core," where API stands for active pharmaceutical ingredient.

The term "inert particle" as used herein includes beads, pellets, spheres, or similar particles that do not contain an active ingredient.

The term "microgranule" as used herein refers to a particle with a mean particle size of not more than about 500 µm. In some embodiments, a microgranule can have a mean particle size of not more than about 400 µm.

The term "Acceptable Long Term Stability" refers to a dosage form that retains at least about 90% of its initial potency, more particularly about 95% and in accordance with certain aspects of the present invention at least about 97% of its potency when the dosage form in a commercial packaging configuration is stored at controlled room temperature conditions, e.g., at 25° C./60% RH for the duration of the shelf life, typically 3 to 5 years.

To determine product shelf-life, dosage forms are stored in commercial packaging configurations in stability chambers per International Conference Harmonization (ICH) guidelines, i.e., at 25° C./60% RH for up to 3-5 years (long-term); at 30° C./65% RH for up to 12 months, and at 40° C./75% RH for up to 6 months. The degradant types and their levels are established, and the specifications for the individual known and unknown impurities as well as for the total impurities are also established and justified in accordance with the ICH guidelines. Studies carried out on impurities of the dosage form that are formed under forced degradation conditions (i.e., 80° C./75% RH, 4 days) could be helpful in the mechanistic evaluation of degradation pathways. In some embodiments, dosage forms having acceptable long term stability may have total impurities of less than about 4%, more specifically less than about 2% and preferably less than about 1% after forced degradation.

The term "low molecular weight polyol" refers to a compound with multiple hydroxyl groups (such as a sugar alcohol or saccharide). In some embodiments, the low molecular weight polyol has a molecular weight of less than about 1000 g/mol, inclusive of less than about 900 g/mol, less than about 800 g/mol, less than about 700 g/mol, less than about 600 g/mol, less than about 500 g/mol, less than about 400 g/mol, less than about 300 g/mol, less than about 200 g/mol, less than about 100 g/mol, etc., including ranges and subranges therebetween.

The term "substantially masks the taste" in reference to the taste-masking layer of the compositions of the present invention refers to the ability of the taste masking layer to substantially prevent release of bitter tasting drug in the oral cavity of a patient. A taste-masking layer which "substantially masks" the taste of the drug typically releases less than about 10% of the drug in the oral cavity of the patient, in other embodiments, less than about 5%, less than about 1%, less than about 0.5%, less than about 0.1%, less than about 0.05%, less than about 0.03%, less than about 0.01% of the drug. The taste-masking properties of the taste-masking layer of the compositions of the present invention can be measured in vivo (e.g., using conventional organoleptic testing methods known in the art) or in vitro (e.g., using dissolution tests as described herein). The skilled artisan will recognize that the amount of drug release associated with a taste-masking layer than "substantially masks" the taste of a drug is not limited to the ranges expressly disclosed herein, and can vary depending on other factors such as the perceived the bitterness of the drug and the presence of other flavoring agents in the composition.

In some embodiments, the present invention provides pharmaceutically acceptable cetirizine compositions in the orally disintegrating tablet (ODT) form exhibiting long-term stability and methods for making taste-masked microparticles and orally disintegrating tablets, which provide long-term stability, effective taste-masking, smooth mouthfeel (little or no aftertaste) as well as rapid, substantially complete release upon reaching the stomach.

In particular embodiments, ODT compositions of the present invention comprising mannitol microgranules containing a substituted benzhydrylpiperazine (e.g., cetirizine), taste-masked with a coating comprising a mixture of a water-insoluble polymer and a gastrosoluble polymer, exhibits an improved long-term stability profile e.g., during commercial distribution to patients requiring such a medication, compared to known substituted benzhydrylpiperazine-containing ODT compositions, such as ODT formulations, prepared by compressing a blend of taste-masked substituted benzhydrylpiperazine (e.g. cetirizine) microgranules and rapidly-dispersing mannitol/crospovidone microgranules in the same matrix, which has been shown to be bioequivalent to both 'IR swallow' and 'Chewable' Zyrtec tablets.

In certain specific embodiments, cetirizine dihydrochloride-containing cores may be taste-masked by fluid-bed coating with a mixture of a water-insoluble polymer, such as ethylcellulose, and a gastrosoluble polymer, such as commercially available gastrosoluble polymers Eudragit® E100 or EPO, at a ratio of from about 95/5 to about 50/50. In other embodiments, the present invention provides a method for preparing stable orally disintegrating tablet formulations comprising taste-masked cetirizine dihydrochloride for oral administration without water. The ODT thus prepared rapidly disintegrates in the oral cavity into a smooth, easy-to-swallow suspension which does not leave any significant aftertaste. Cetirizine is rapidly released upon entry into the stomach for rapid systemic absorption, thereby enhancing the probability of being bioequivalent to the Zyrtec brand product. The taste-masked composition prepared in accordance with the present invention rapidly releases the drug, i.e., not less than about 75% of the dose released in 15 minutes when tested for dissolution using United States Pharmacopoeia Apparatus 1 (baskets @ 100 rpm) or 2 (paddles @ 50 rpm) in 900 mL of 0.1N HCl.

In another embodiment, the present invention is directed to a composition comprising a core particle comprising a substituted benzhydrylpiperazine or a pharmaceutically acceptable salt, ester, and/or solvate thereof, coated with a taste-masking layer comprising a water-insoluble polymer and a gastrosoluble polymer, wherein the core particle comprises an inert particle layered with the drug. In another embodiment, the drug-layered, taste-masked core particles are mixed with rapidly dispersing granules containing polyols (e.g., sugar alcohols) and incorporated into an orally disintegrating dosage form. In another embodiment, the orally disintegrating dosage form shows acceptable long-term stability, as evaluated by normal storage conditions, accelerated stability studies, or forced degradation studies. Without being bound by any hypothesis on the mechanism of stabilization, the taste-masking layer comprising a water-insoluble polymer and a gastrosoluble polymer provides a flexible membrane that can minimize or substantially eliminate potential membrane fracture during compression to form the dosage form. An intact (unfractured) membrane is expected to minimize or substantially eliminate direct contact between the substituted benhydrylpiperazine and the polyoyl of the rapidly dispersing granules.

Surprisingly, substituted benzhydrylpiperazine-containing inert particles (e.g., cetirizine-containing inert particles) layered with a taste-masking layer (e.g., ethylcellulose and Eudragit® E100) incorporated into an orally disintegrating dosage form show improved long-term stability compared to known benzhydrylpiperazine-containing ODT compositions. It is hypothesized that the taste-masking membrane coating the core particle remains intact during the compression step, thereby minimizing or substantially eliminating contact between the drug and polyol (e.g., sugar alcohol). In contrast, when the core particle comprises drug-containing microgranules, the drug in microgranules may come into contact with the polyol of the rapidly dispersing granules, due to minor membrane fracture that can occur during compression of the formulation on the tablet press.

The multi-particulate compositions in accordance with one embodiment of the invention comprise taste-masked core particles (drug crystals or drug-containing granules, beads or pellets) comprising one or more bitter-tasting substituted benzhydrylpiperazines produced by fluid-bed coating with a flexible membrane comprising a mixture of water-insoluble ethylcellulose and gastrosoluble Eudragit E100. Without being bound by any hypothesis on the mechanism of stabilization, the membrane comprising a combination of ethylcellulose and Eudragit E100 is highly flexible and such a flexible membrane is expected to substantially eliminate or minimize potential membrane fracture during compression of taste-masked substituted benzhydrylpiperazine (e.g., cetirizine) with mannitol/crospovidone microgranules, thereby eliminating or minimizing direct contact between the substituted benzhydrylpiperazine (e.g., cetirizine) and mannitol.

Another specific embodiment of the invention relates to a method of preparing a compression mix by blending together taste-masked substituted benzhydrylpiperazine (e.g., cetirizine) microparticles, rapidly dispersing microgranules and other pharmaceutically acceptable excipients including flavors, a sweetener(s), and optionally colorants, a disintegrant, microcrystalline cellulose, but substantially free of lubricant and compressing into orally disintegrating tablets using a conventional rotary tablet press and externally lubricated dies and punches in accordance with the disclosures in U.S. Pat. Nos. 5,700,492; 6,062,826; and 6,964,779, the contents of which are hereby incorporated by reference in their entirety for all purposes. These orally disintegrating tablets having very minute quantities of the of lubricant confined largely on or near the surface, exhibit the properties of disintegrating on contact with saliva in the buccal cavity within about 60 seconds forming a smooth easy-to-swallow suspension with no aftertaste (good, creamy mouthfeel) and rapidly releasing the drug dose upon entry into the stomach, thus providing substantial bioequivalence with the reference product.

These and other embodiments, advantages and features of the present invention become clear when detailed description and examples are provided in subsequent sections.

Unless indicated otherwise, all percentages and ratios are calculated by weight. Unless indicated otherwise, all percentages and ratios are calculated based on the total composition.

One or more substituted benzhydrylpiperazines such as cetirizine may be taste-masked by fluid-bed coating in accordance with the method of manufacturing disclosed in a co-pending U.S. patent application Ser. No. 11/248,596, filed Oct. 12, 2005 (U.S. Pub. No. 2006/0078614), the contents of which are hereby incorporated by reference in their entirety for all purposes. Microparticles (drug crystals, drug-containing granules, beads or pellets) may be provided with a flexible taste-masking membrane comprising a combination of a water-insoluble polymer and a gastrosoluble polymer at a ratio of from about 95/5 to about 30/70.

Specific embodiments of the invention will be described in further detail with reference to the accompanying FIG. 1. FIG. 1 shows an API-core comprising a drug crystal, a pellet, a microgranule or an inert particle layered with a drug substance requiring taste-masking. This API core is then coated with a taste-masking layer comprising a water-insoluble polymer in combination with a gastrosoluble pore-former, a gastrosoluble polymer such as Eudragit E100. In the dry state and even when placed in the buccal cavity, the pore-former is insoluble and typically no drug or minimal drug is released from the taste-masked particle. However, upon entering the stomach, the gastrosoluble pore-former rapidly dissolves creating microchannels through which the drug is rapidly released. In one embodiment, the composition of the invention comprises (a) a core particle comprising a substituted benzhydrylpiperazine or a pharmaceutically acceptable salt, ester, and/or solvate thereof; and (b) a taste-masking layer comprising a water-insoluble polymer and a gastrosoluble polymer, wherein said taste-masking coating layer effectively masks the taste of the substituted benzhydrylpiperazine or a pharmaceutically acceptable salt, ester, and/or solvate thereof.

In another embodiment, the composition further comprises a seal-coating layer surrounding the core particle, underneath the taste-masking layer. In another embodiment, the seal-coating layer comprises hydroxypropyl methylcellulose. Low-viscosity hydroxypropyl cellulose, commercially available from Colorcon as Opadry® Clear, is suitable for the seal-coating layer.

An aqueous or a pharmaceutically acceptable solvent medium may be used for preparing drug containing core particles for taste-masking, e.g., inert cores such as sugar spheres, cellulose or silicon dioxide spheres layered with a drug in fluid-bed or pan-coating equipment. The drug layer can optionally contain a film forming binder. The type of film forming binder that is used to bind the water-soluble drug to the inert sugar sphere is not critical but usually comprises a water-soluble, alcohol-soluble or acetone/water soluble polymeric binder. A polymeric binder may be used at concentrations of about 0.5 to 10 weight % based on the drug-layered beads. The drug substance may be present in this coating formulation in solution form or may be suspended at a solid content up to about 35% depending on the viscosity of the coating formulation.

Crystals of a bitter substituted benzhydrylpiperazine, such as cetirizine dihydrochloride, with a desired particle size range (in some embodiments from about 20 μm to 400 μm, in other embodiments from about 50 μm to 300 μm) may be taste-masked directly. Alternatively, microgranules containing milled or micronized drug particles may be produced by granulating the drug and a suitable filler/diluent with an (optional) polymeric binder (which imparts resilient characteristics to the dried microgranules to resist attrition due to fluidization during fluid-bed coating with the taste-masking composition), in a high-shear granulator.

Examples of specific useful polymeric binders include polyvinylpyrrolidone (PVP), hydroxypropylcellulose (e.g., Klucel® LF from Aqualon), modified starch (e.g., Starch 1551 commercially available from National Starch), Kollidon® VA 64, poly(vinyl acetate-vinylpyrrolidone) from BASF, hydroxypropyl methylcellulose (e.g., with a viscosity of 400 cps or less, such as Methocel and Metolose commercially available from Dow Chemical and Shin Etsu Chemicals) alone or in combination thereof. Examples of fillers include lactose and microcrystalline cellulose. Typically, microgranules prepared in accordance with this embodiment of the invention can contain from about 20% to about 90% of the drug, and up to about 15% binder with any optional filler/diluent being present at from about 0% to 80% by weight of the microgranules.

Water-insoluble polymers suitable for the taste-masking layer include ethylcellulose, cellulose acetate, cellulose acetate butyrate, and methacrylate copolymers available under the trade name of Eudragit® (type RL, RS and NE30D).

Gastrosoluble polymers suitable for the taste-masking layer include maltodextrin (e.g., sold under the tradename Maltrin®), neutral methacrylic acid-methylmethacrylate copolymers, neutral copolymers based on ethyl acrylate and methylmethacrylate (e.g., available under the trade name of Eudragit® E100 (granule form) or Eudragit® EPO (powder form)), polyvinylacetal diethylaminoacetate (e.g., AEA® available from Sankyo Company Limited, Tokyo, Japan), and the like. In one embodiment, the gastrosoluble polymer is a terpolymer based on dimethylaminoethyl methacrylate, butyl methacrylate, and methyl methacrylate. In another embodiment, the terpolymer has an average molecular weight of 150,000 and the ratio of the monomers is 1:2:1 of methyl methacrylate, N,N-dimethylaminoethyl methacrylate, and butyl methacrylate.

In one embodiment, the ratio of water-insoluble polymer to gastrosoluble polymer in the taste-masking layer may typically vary from about 95/5 to about 30/70. In another embodiment, this ratio ranges from about 80/20 to about 50/50. In a particular embodiment, the water-insoluble polymer is ethylcellulose with a viscosity of about 7-100 cps when tested as a 2 weight % aqueous solution at ambient temperature.

In another embodiment, the taste-masking layer comprises from about 5% to about 50% by weight of the taste-masked, drug-containing core particle. In another embodiment, the taste-masking layer ranges from about 10% to about 30% by weight of the taste-masked, drug-containing core particle.

The taste-masking layer described herein may be free of plasticizers, or contain one or more optional plasticizers. Representative examples of suitable plasticizers include triacetin, polyethylene glycol, tributyl citrate, triethyl citrate, acetyl tri-n-butyl citrate, diethyl phthalate, castor oil, dibutyl sebacate, acetylated monoglycerides and the like or mixtures thereof. In one embodiment, the plasticizer comprises an acetylated monoglyceride. Acetylated monoglycerides are typically made by reacting fats with glycerine and triacetin. In another embodiment the plasticizer comprises an acetylated monoglyceride where the fat source is partially hydrogenated soybean oil (e.g., Myvacet® 9-45). Acetylated monoglycerides are sold in the United States under the tradename "Myvacet" by Eastman Chemical Products Inc. The plasticizer may typically comprise about 3-30% or about 5-15% of the taste-masking layer, based on the weight of dry polymer.

The taste-masking layers described herein may also include one or more lubricating agents, such as magnesium stearate, talc, stearic acid, glyceryl behenate, a hydrogenated vegetable oil, polyethylene glycol, etc. The taste-masking layer may also include anti-tacky agents. Representative examples of anti-tacky agents that may be used include, without limitation, talc and magnesium stearate.

The ODT compositions described herein typically comprise rapidly-dispersing microgranules. The rapidly-dispersing microgranules may be produced as described in co-pending U.S. patent application Ser. No. 10/827,106, filed Apr. 19, 2004 (U.S. Pub. No. 2005/0232988), the entire contents of which are hereby incorporated by reference for all purposes. The rapidly-dispersing microgranules comprise one or more sugar alcohols, saccharides or mixtures thereof, and a disintegrant which are typically prepared by granulation in a high-shear granulator and dried in a convection oven or in fluid bed equipment Examples of suitable sugar alcohols include mannitol, sorbitol, xylitol, maltitol and the like. Examples of disintegrants include crospovidone (crosslinked PVP), sodium starch glycolate, crosslinked sodium carboxymethyl cellulose, and low substituted hydroxypropylcellulose, each of which has an average particle size of not more than about 30 μm. The relative amounts of polyols (e.g., sugar alcohols) and the disintegrant may vary considerably. Typically, such microgranules will contain from about 80% to about 95% polyol, and from about 5% to about 20% disintegrant, more particularly from about 90% to about 95% polyol and from about 5% to about 10% disintegrant.

A compression mix is prepared in accordance with a certain embodiment of the present invention by blending together taste-masked substituted benzhydrylpiperazine (e.g., cetirizine) containing microparticles, rapidly dispersing microgranules and other pharmaceutically acceptable excipients used in orally disintegrating tablets. Examples of pharmaceutically acceptable excipients include flavors, a sweetener(s), and optionally colorants, disintegrants, microcrystalline cellulose, etc. In accordance with certain embodiments, the compression mix may be substantially free of lubricant. The ratio of taste-masked substituted benzhydrylpiperazine (e.g., cetirizine) containing to rapidly dispersing microgranules may vary significantly. Typically the ratio of taste-masked particles to rapidly dispersing microgranules varies from about 1/1 to 1/10 by weight, more particularly from about 1/3 to 1/8 by weight.

Orally disintegrating tablets are compressed in accordance with a certain embodiment of the present invention using a conventional rotary tablet press and externally lubricated dies and punches in accordance with the disclosures in U.S. Pat. No. 5,700,492 and U.S. Pat. No. 6,776,361, the entire contents of which are hereby incorporated by reference for all purposes.

One method of producing taste-masked microparticles (mean particle size of about 100-400 μm) comprising one or more bitter substituted benzhydrylpiperazines comprises (i) preparing drug-containing microparticles (e.g., crystals with a desired average particle size range for example from about 50 μm to 300 μm, microgranules, drug-layered beads or extruded/spheronized pellets) and (ii) coating these drug-containing microparticles with ba taste-masking layer. Drug-layered beads may be prepared by dissolving or suspending one or more active pharmaceutical ingredients (and optionally a polymeric binder) in a pharmaceutically acceptable solvent, and layering the drug onto inert particles such as sugar spheres (e.g., Celphere, 50-100 mesh or 150-300 μm) using a fluid-bed coater equipped with a bottom-spray Wurster insert. Resilient drug-containing microgranules, which undergo little or minimal attrition during membrane coating in fluid-bed equipment, may be prepared by granulating one or more actives and a filler or diluent (if needed) with a polymeric binder solution in a high-shear granulator. Drug-containing beads may also be produced by granulating the drug in a high-shear granulator as described above, followed by extrusion and spheronization of the wet mass using extrusion-spheronization equipment.

Another method of producing taste-masked microparticles (crystals, microgranules, drug-layered beads or extruded/spheronized pellets) in accordance with another embodiment of the invention comprises fluid-bed coating with a mixture of a water-insoluble polymer such as ethylcellulose or polyvinyl acetate and a gastrosoluble polymer such as Eudragit E100 or AEA® (polyvinylacetal diethylaminoactate) at a ratio of 50/50 to 95/5, thereby providing a weight gain of from about 5% to about 50%, preferably from about 10% to about 30%. One embodiment of the invention comprises dissolving 46.3/46.3 ethylcellulose/E100 in 95/5 acetone/water with a plasticizer (e.g., Myvacet 9-45 at about 10% of the weight of ethylcellulose), suspending micronized talc therein, and then coating the resulting solution/suspension onto the drug-containing cores (crystals, drug-layered beads, microgranules or pellets) in a fluid-bed coater equipped with a bottom-spray Wurster insert.

The invention also provides a method of manufacturing single-layer orally disintegrating tablets comprising taste-masked substituted benzhydrylpiperazine (e.g., cetirizine dihydrochloride) and rapidly-dispersing microgranules, which exhibit acceptable long-term stability, even though the polyol (e.g., mannitol) is present in the same layer with the substituted benzhydrylpiperazine.

In accordance with certain other embodiments of the invention, the method of manufacturing stable orally disintegrating tablets comprises the following steps:
a) preparing a drug containing core particle by (i) drug-layering on an inert particle (e.g., a 50-100 mesh sugar sphere or cellulose sphere, such as Celphere®) from a solution/suspension comprising a polymeric binder and the drug in a fluid-bed coater and optionally applying a protective seal-coat, or (ii) granulating the drug and a diluent such as lactose and/or microcrystalline cellulose with a polymeric binder, or (iii) granulating as in (ii) above, followed by extrusion and spheronization;
b) coating drug containing core particles with a solution comprising a water insoluble polymer and a gastro-soluble polymer, thereby providing taste-masked microparticles with a desired particle size distribution (e.g., an average particle size of not more than about 400 µm, more particularly not more than about 350 µm);
c) granulating a sugar alcohol or a saccharide, or a combination thereof, each of which has an average particle diameter of not more than about 30 µm, with a disintegrant such as Crospovidone using water or an alcohol-water mixture in a granulator and drying with fluid bed equipment to produce rapidly-dispersing microgranules with an average particle size not more than about 400 µm (typically with an average particle size of not more than about 300 µm);
d) blending taste-masked microparticles of step (b) with rapidly disintegrating microgranules of step (c) and optionally other acceptable ingredients such as a flavoring agent, a coloring agent, a sweetener and additional disintegrant in sufficient quantities; and compressing into tablets using a conventional rotary tablet press equipped with an external lubrication system to pre-lubricate the dies and punches.

In Vitro Dissolution Testing:

The taste-masking property of the taste-masked microparticles and the orally disintegrating tablets in the mouth is evaluated by determining the percentage of drug-release (a release of not more than 10% of the dose in about 3 minutes is considered acceptable) when tested for dissolution using USP Apparatus 1 (baskets @ 100 rpm) or Apparatus 2 (paddles @ 50 rpm) in 900 mL of simulating saliva fluid at a pH of about 6.8. Further, the rapid-release property in the stomach of the taste-masked microparticles and the orally disintegrating tablets is evaluated by determining the percentage of drug-release (a release of not less than 75% of the dose in about 30 minutes is considered acceptable) when tested for dissolution using USP Apparatus 1 (baskets @ 100 rpm) in 900 mL of simulated gastric fluid or 0.1N HCl (at pH 1.2).

The following non-limiting examples illustrate the pharmaceutically acceptable, patient-friendly, orally disintegrating tablet compositions comprising one or more extremely bitter active substances belonging to the substituted benzhydrylpiperazine family and rapidly-dispersing microgranules comprising one or more polyols, manufactured in accordance with the invention, which exhibit not only acceptable taste-masking when placed in the mouth and substantially complete, rapid release of the dose on entry into the stomach, but also acceptable long-term stability.

EXAMPLES

Example 1

Cetirizine.2 HCl IR Beads (drug load: approximately 8% by weight): Cetirizine dihydrochloride (180 g) was slowly added to an aqueous solution (15.7 g of polyvinylpyrrolidone {Povidone K-29/32} in 782.8 g of purified water) and mixed well. 60-80 mesh (177-250 µm) sugar spheres (1,900 g) were spray-coated with the drug-layering formulation in a Glatt fluid bed granulator, GPCG 3 equipped with a bottom spray Wurster insert. The drug containing beads were dried, and a seal coat of Opadry Clear (42.8 g) was applied. The drug load was measured to be 8.4% by weight.

Figure 2:
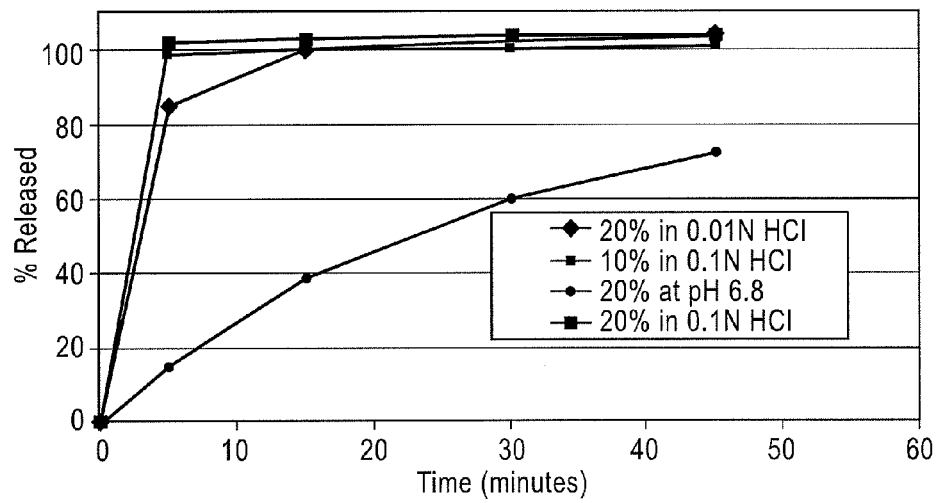
FIG. 2 demonstrates the dissolution profiles for orally disintegrating tablets of Example 1 comprising cetirizine dihydrochloride taste-masked by fluid-bed coating with ethylcellulose and Eudragit E100 at a ratio of 50:50 when dissolution tested in 0.1N HCl, 0.01N HCl, or at pH 6.8 in United States Pharmacopeia Apparatus 1 (paddles at 100 rpm, 900 mL buffer).
Figure 3:
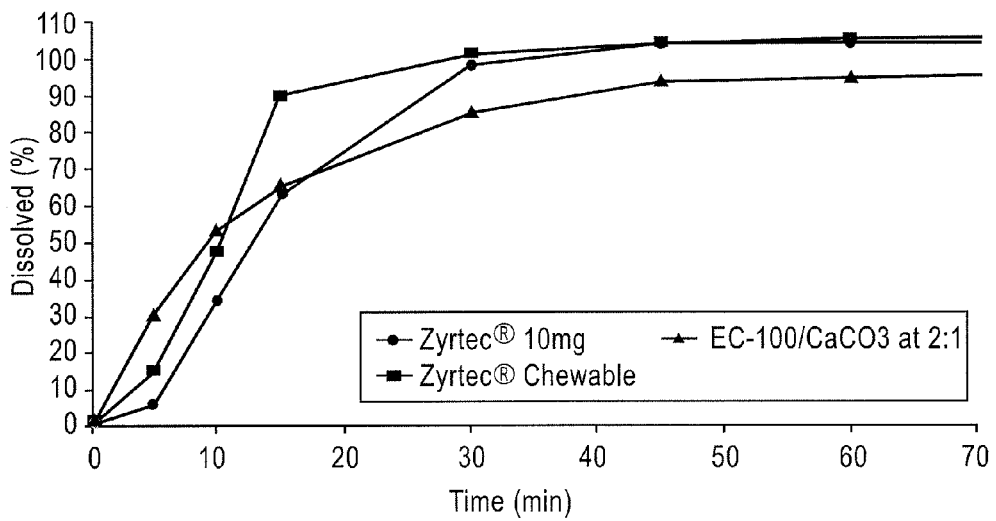
FIG. 3 demonstrates the dissolution profiles for Zyrtec® tablets, Zyrtec® Chewable tablets, and orally disintegrating tablets of Example 4 comprising cetirizine dihydrochloride taste-masked by solvent coacervation with ethylcellulose and calcium carbonate. Dissolution conditions are USP Apparatus 2 (paddles at 50 rpm) in 900 mL of 0.1N HCl at 37° C.

Taste-masked Cetirizine.2 HCl Beads: The drug-layered beads (1200 g) prepared as described above were coated with a solution of Ethylcellulose (Ethocel Standard Premium 10 cps)/Eudragit E100 at a ratio of 46.3/46.3 with Myvacet 9-45 (plasticizer)/talc at a ratio of 4.62/2.78 dissolved in 95/5 acetone/water for a 20% weight gain. Samples were pulled during the coating process at a weight gain of about 10% and 15% and tested for dissolution to examine the effect of coating level on dissolution as well as organoleptic properties. The coated beads were dried/cured at 60° C. for 10 minutes in the Glatt GPCG unit and sieved to discard agglomerates. FIG. 2 shows the dissolution profiles in 0.1N HCl from taste-masked microcapsules coated at 10% and 20%. The figure also shows the dissolution from the 20% coated microcapsules when tested in the phosphate buffer at pH 6.8 simulating the saliva pH.

Rapidly Dispersing Microgranules: Rapidly dispersing microgranules comprise a sugar alcohol such as mannitol, a saccharide such as lactose, or a combination thereof, and a disintegrant such as Crospovidone. The sugar alcohol and disintegrant will typically be present in the rapidly dispersing microgranules at a ratio of from about 99:1 to about 90:10 (sugar alcohol:disintegrant). For example, D-mannitol, a sugar alcohol with an average particle size of about 15 µm and Crospovidone XL-10, a super disintegrant, were granulated at a ratio of about 95/5 in a high shear granulator using purified water as the granulating fluid, and tray dried in a convection oven for an LOD (loss on drying) of about 0.5% by weight. The dried granules were sieved using an appropriate sieve and a Kason siever, and the oversized granules were milled using a Fitzmill to produce rapidly dispersing granules with an average particle size of less than 400 µm.

Cetirizine Dihydrochloride ODT, 10 mg (1153-BLY-017): 20% coated beads (15 g) and rapidly-dispersing microgranules, prepared as above, (46.4 g) were blended with Crospovidone XL-10 (2.6 g), peppermint flavor (0.6 g), and Sucralose (0.4 g) before compressing into 10 mg orally disintegrating tablets (13 mm in diameter) weighing approximately 650 mg with an average hardness of 35 N. The tablets thus produced would exhibit a smooth taste in the oral cavity disintegrating in about 30 seconds and drug-release in excess of 95% in 15 min when dissolution tested in 0.1N HCl.

Example 2

Cetirizine.2 HCl ODT, 10 mg: 20% coated beads (33.4 g) and rapidly-dispersing microgranules, prepared as in Example 1, (61.1 g) were blended with Crospovidone XL-10 (4 g), strawberry flavor (0.9 g), and Sucralose (0.6 g) before compressing into 10 mg orally disintegrating tablets weighing approximately 450 mg with an average hardness of 30 N. The tablets thus produced exhibit an acceptable taste in the oral cavity disintegrating in about 30 seconds and drug-release in excess of 95% in 15 min when dissolution tested in 0.1N HCl.

Example 3

Cetirizine.2 HCl IR Beads (drug load: 8.4% by weight): Cetirizine dihydrochloride (336.7 g) was slowly added to an aqueous solution (29.4 g of hydroxypropylcellulose (Klucel LF, a binder) in 1463.9 g of purified water) and mixed well. 60-80 mesh sugar spheres (3553.7 g) were spray-coated with the drug-layering formulation in a Glatt fluid bed granulator, GPCG 5 equipped with a 9" (diameter) bottom spray Wurster column (10" partition height)) with the following parameters and conditions:—nozzle port size: 1.0 mm; bottom air distribution plate: 'B' covered with 15 gauge 100-mesh product retention screen; atomization air pressure: 2.0 bar; inlet temperature: 53° C.; product temperature: 45° C.; fluidization air volume: 80-90 CFM; spray rate ramped up from 5 mL/min to 10 mL/min. Following completion of drug layering, the beads were applied a seal coat of 2% hydroxypropylmethylcellulose (Opadry Clear, 80.2 g) and dried in the unit for 5 min to drive off excess moisture.

Taste-masked Cetirizine.2 HCl Beads: The drug-layered beads prepared above (3300 g) were coated with a solution of Ethylcellulose (EC-10; 371.94 g)/Eudragit E100 (329.31 g) with Myvacet® 9-45 (41.25 g) and magnesium stearate (82.5 g) dissolved/dispersed in 48.5/24/27.5 acetone/IPA/water (8094 g) for 20% weight gain at the product temperature of 42-43° C., air volume of 55 CFM and spray rate ramped up from 4 mL/min to 21 mL/min. The coated beads were dried/cured at 43° C. for 5 minutes in the Glatt GPCG unit and sieved to discard agglomerates.

Cetirizine Dihydrochloride ODT, 10 mg dose: 1560 g of taste-masked microparticles and 1762 g of rapidly dispersing microgranules, prepared as in Example 1, were blended with 400 g of microcrystalline cellulose (Avicel PH101), 200 g of crospovidone, 64 g of strawberry flavor, and 14 g of Sucralose (a sweetener) in a V-blender and compressed into tablets (13 mm in diameter) with an average weight of 450 mg and average hardness of about 37 N and friability of 0.24% to demonstrate robustness of the manufacturing (taste-masking and tabletting) process and meeting target dissolution specifications (not more than about 10% in 5 minutes in the simulated saliva fluid at pH 6.8 and not less than about 75% released in 15 minutes in 0.1N HCl).

Example 4

Cetirizine Microgranules (drug load: approximately 20% cetirizine dihydrochloride): Cetirizine dihydrochloride (20%), microcrystalline cellulose (70%) and hydroxypropyl methylcellulose (Methocel K100LV at 10% by weight) were granulated with purified water in a high-shear granulator and dried in a tray-drying oven.

Taste-masked Microgranules (drug load: approximately 12% cetirizine dihydrochloride): Cetirizine Microgranules (700 g) prepared as described above with a low friability (less than 15% by weight when tested in accordance with procedure disclosed in U.S. patent application Ser. No. 10/827,106 with a priority date of Apr. 19, 2004 which is incorporated by reference in its entirety), obtained as described above were microencapsulated using a solvent coacervation process (described in U.S. patent application Ser. No. 11/213,266, filed on Aug. 25, 2005). Ethocel (ethylcellulose) Standard 100 Premium (100 cps), from Dow Chemicals (300 g) was dissolved in a 5-gallon coacervation tank at 80° C. A micronized pore-former (150 g calcium carbonate) was added into the coacervation tank at a product temperature of approximately 58° C. during the temperature-programmed cooling cycle to achieve a uniform distribution of the pore-former throughout the ethylcellulose membrane. Upon reaching the ambient temperature, the microcapsules with a membrane coating of 2/1 ethylcellulose/calcium carbonate at approximately 39% by weight were filtered, washed with fresh cyclohexane and dried to reduce the residual solvent level to within acceptable limits. The taste-masked microparticles with an average particle size of 230 µm had an acceptable taste.

Rapidly Dispersing Microgranules: The rapidly dispersing microgranules may comprise a sugar alcohol such as mannitol and/or a saccharide such as lactose and a disintegrant such as Crospovidone. The sugar alcohol and/or saccharide and disintegrant will typically be present in the rapidly dispersing microgranules at a ratio of from about 99:1 to about 90:10 (sugar alcohol and/or saccharide:disintegrant). For example, the rapidly dispersing microgranules used in the ODT formulations disclosed in the various examples in accordance with the present invention were produced by granulating 95 parts of D-mannitol with an average particle size of about 15 µm, and 5 parts of crospovidone in a high shear mixer with water as the granulating fluid, drying the wet mass in a tray drying oven or a fluid bed dryer, and sieving/milling to obtain granules with an average particle size of less than 400 µm.

Cetirizine Dihydrochloride ODT, 10 mg (as cetirizine dihydrochloride): 81 mg of taste-masked microparticles and 529 mg of rapidly-dispersing microgranules, prepared as described above, were blended with 32.5 mg of crospovidone, 6.5 mg of an orange flavor, 0.65 mg of Sucralose (a sweetener) and compressed into tablets (13 mm (diameter)× 4.68 mm) with an average weight of 650 mg and average hardness of 97 N and friability of 0.5% to demonstrate robustness of the manufacturing (taste-masking and tableting) process and meeting target dissolution specifications (not more than about 10% in 5 minutes in the simulated saliva fluid at pH 6.8 and not less than about 75% released in 30 minutes in 0.1N HCl).

Example 5

Stability of Cetirizine Dihydrochloride (10 mg) Formulations under Accelerated Stability Conditions Cetirizine is known to have significant chemical interactions with common tablet excipients. ODTs of Example 4 and commercial products (Zyrtec® IR tablets (lot#0183K03A) and Zyrtec Chewable tablets (lot#08254V)) were subjected to forced degradation conditions, i.e., at 80° C./75% RH (relative humidity). Their stability performance values are presented in Table 1. The tablets of Example 4 show a significant reduction in potency with increasing storage time at accelerated stability conditions, i.e., at 40° C./75% RH. The commercial tablets (Zyrtec® and Zyrtec® Chewable) exhibit minor reductions. In contrast, the ODTs of Example 1 exhibit no significant reduction in potency.

TABLE 1

Stability of Cetirizine Formulations

Stability Performance at Accelerated Stability Conditions:
(% Dissolved of Label Claim of 10.0 mg)*

| Stability Timepoint | Cetirizine ODT (Example 1) | Cetirizine ODT (Example 4) | Zyrtec ® | Zyrtec Chewable, 10 mg |
|---|---|---|---|---|
| Initial | 101.9 | 102.8 | 100% | 100% |
| 1 month at 40° C./75% RH* | 100.9 | 102.0 | 99.7 | 98.9 |
| 3 months at 40° C./75% RH | 101.7 | 93.8 | 99.1 | 97.9 |
| 6 months at 40° C./75% RH | 100.3 | 85.0 | 97.2 | 96.2 |

*Stability performance values in % label claim wherein 100% label claim = 10.0 mg ceterizine dihydrochloride.
**RH refers to relative humidity.

Stability performance values were determined according to the results of a dissolution assay. The cetirizine dihychloride formulations of Table 1 were tested for initial dissolution (% dissolved relative to the label claim of 10 mg for the Zyrtec® and Zyrtec® Chewable tablets). Dissolution was carried out using USP Apparatus 2 (paddles at 50 rpm) in 900 mL of 0.1N HCl. The amount dissolved was determined by the area under the peak in HPLC. The tablets were then stored for six months under accelerated stability conditions (i.e., 40° C. at 75% RH) and subjected to the dissolution assay at one-month, three-month, and six-month time points.

Example 6

Figure 4:
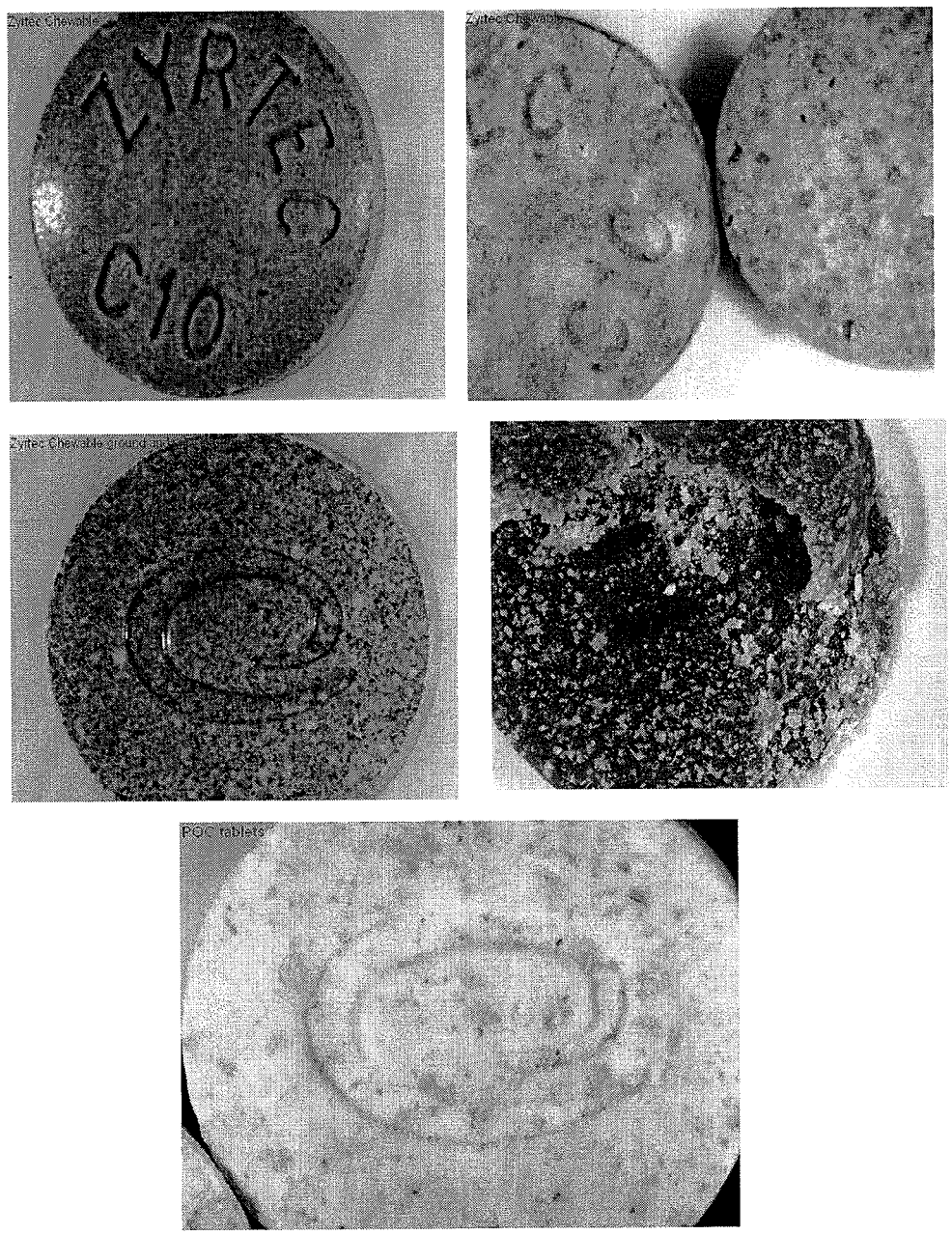
FIG. 4 demonstrates the micrographs of Zyrtec IR tablets (top left: Initial; top right: Stressed), Zyrtec Chewable tablets (middle left: Initial; middle right: Stressed), and orally disintegrating tablets of Example 4 comprising cetirizine dihydrochloride taste-masked by solvent coacervation with 2/1 ethylcellulose/calcium carbonate (bottom: Stressed). The "stressed" pictures represent after 4 days under forced degradation conditions (80° C./75% relative humidity).

Stability of Cetirizine Dihydrochloride Formulations under Forced Degradation Conditions: Several forced degradation studies were conducted (80° C./75% RH, 4 days) on Zyrtec®, Zyrtec® Chewable and Cetirizine ODT (Example 4). The results are shown in FIG. 4. These forced degradation conditions are a predictive guide to normal accelerated study conditions at the 3- to 6-month time point. Although color change is not necessarily a reliable measure of chemical impurity levels, the reference products, as well as ODTs of Example 4, did exhibit significant degradation (in the range of 4-6%), as determined by measuring the sum total of the peak areas of all individual known and unknown degradants in the HPLC relative to the peak area of cetirizine dihydrochloride). Furthermore, the same impurities appeared in comparable amounts. In contrast, the taste-masked microcapsules exhibited a total impurity of about 1.47% at forced degradation conditions suggesting that significantly higher total impurity levels in the tablet formulations were due to incompatibility between cetirizine and the tableting excipients.

At the accelerated stability conditions (i.e., 40° C./75% RH) at 6-month time point, both marketed products exhibited total impurities of about 1.0%. while the cetirizine ODT of Example 4 exhibited total impurities of the order of 5%. In contrast, Cetirizine ODT of Example 1 showed very little color change, insignificant changes in the potency and comparatively lower total impurities.

These forced degradation studies were performed to characterize degradation products that could be observed in cetirizine dosage forms: Zyrtec® (Zyrtec IR) tablets, Zyrtec chewable tablets, as well as cetirizine ODT tablets, during long-term storage or on accelerated stability. Formation of intense discoloration in these micrographs (e.g, intensely colored specks) suggest significant degradation caused by the interaction of cetirizine with a sugar alcohol under those conditions. The presence of discolored specks in the cetirizine ODT tablets of Example 4 stored in induction sealed high density polyethylene (HDPE) bottles at 40° C./75% RH (relative humidity) at the 3- and 6-month time points was confirmed. In contrast, orally disintegrating tablets comprising cetirizine dihydrochloride fluid-bed coated with ethylcellulose/Eudragit E100 stored in induction-sealed high-density polyethylene (HDPE) bottles at 40° C./75% RH (relative humidity) for 6 months showed no colored specks (not shown in FIG. 4).

Example 7

Cetirizine.2 HCl IR Beads (drug load: 11.4% by weight): Cetirizine dihydrochloride (227.8 g) was slowly added to an aqueous solution containing 20 g of hydroxypropylcellulose (Klucel LF, a binder) in 991.2 g of purified water and mixed well. 60-80 mesh sugar spheres (1712.2 g) were spray-coated with this drug-layering formulation in a Glatt fluid bed granulator, GPCG 3 equipped with a bottom spray Wurster insert. The processing parameters and conditions: nozzle port size: 1.0 mm; bottom air distribution plate: 'C', atomization air pressure: 1.5 bar; inlet temperature: 61° C.; product temperature: 45° C.; fluidization air volume: 53-60 CFM; spray rate: from 3 mL/min ramped up to 11 mL/min. Following completion of drug layering, the beads were applied a seal coat of 2% hydroxypropylmethylcellulose (Opadry Clear, 40 g) and dried in the unit for 5 min to drive off excess moisture.

Taste-masked Cetirizine*2 HCl Beads: Cetirizine 2HCl_The drug-layered beads (1500 g) were coated with a solution of ethylcellulose (EC-10; 365.28 g)/Eudragit E100 (323.2 g) with Myvacet 9-45 (40.49 g) and magnesium stearate (45.49 g) dissolved/dispersed in 48.5/24/27.5 acetone/IPA/water for 34% weight gain at the product temperature of 42-43° C., air volume of 55 CFM and spray rate ramped up from 4 mL/min to 21 mL/min. The coated beads were dried/cured at 43° C. for 5 minutes in the Glatt GPCG unit and sieved to discard agglomerates.

Cetirizine Dihydrochloride ODT, 10 mg: 903.67 g of taste-masked microparticles and 2418.4 g of rapidly-dispersing microgranules (comprising mannitol and crospovidone at a ratio of 95/5) were blended with 400 g of microcrystalline cellulose (Avicel PH101), 200 g of crospovidone, 64 g of strawberry flavor, and 14 g of Sucralose (a sweetener) in a V-blender and compressed into tablets (13 mm in diameter) with an average weight of 650-653 mg and average hardness of 29-31 N and friability of 0.22-0.39% using a rotary tablet press equipped with an external lubrication system to lubricate the die and punch surfaces prior to each compression to demonstrate robustness of the manufacturing (taste-masking and tabletting) process and a dissolution of 100% (meeting target dissolution specifications of not less than about 75% released in 15 minutes in 0.1N HCl).

Stability Monitoring of Cetirizine ODT and Placebo ODT: The flavor component in the ODT formulation typically undergoes some changes producing transient degradation products. In order not to include these transient flavor-related degradation products in the total degradants associated with the drug, a placebo ODT batch was also prepared by layering Klucel LF and Opadry Clear onto 60-80 mesh sugar spheres, taste-masking these placebo beads by coating with ethylcellulose EC-10/Eudragit E100, blending with rapidly dispersing granules, strawberry flavor etc. and compressing the blend into tablets. The bulk tablets from above (Cetirizine ODT lot#1254-055 and Placebo ODT lot#1254-053) were packaged in clear 200/02 Aclar blisters (Cetirizine ODT lot# S9A235 and Placebo ODT lot# S9A244) and 250/60 PVC/PVdC opaque blisters (Cetirizine ODT lot# S9A239 and Placebo ODT lot# S9A240) and placed on stability at 25° C./60% RH, 30° C./65% RH, and 40° C./75% RH for 1, 3, and 6 months.

Table 2 shows the comparative stability data for Cetirizine 2HCl ODT tablets—initial versus at the 3-month time point. The Aclar blister as used in this example is less permeable to moisture than the PVC/PVdC, as evident from the moisture increase data at 40° C./75% RH. The cetirizine seems to be equally (if not more) sensitive to light, heat and/or moisture, as evident from the higher degradation observed in the product packaged in Aclar blister than in PVC/PVdC blister at the same stability conditions. In the PVC/PVdC packaging configuration, the observed total impurities at the accelerated stability condition, i.e., at 3-month time point at 40° C./75% RH do not seem to be statistically different from that observed initially, thus demonstrating the improved stability of the compositions of the present invention in which the taste-masked cetirizine dihydrochloride drug particles coexist with mannitol granules in the tablet matrix, even though the drug and the low molecular weight polyol are known to interact. The data in Table 2 also show that the stability of the cetirizine ODT formulation can be further improved by packaging the ODT tablets in induction-sealed HDPE (high density polyethylene) bottles and/or in opaque 200/02 Aclar blisters which protect the tablets from both moisture and light.

TABLE 2

Stability data for Ceirizine Dihydrochloride ODTs in Blister Packs

| Parameter | Initial | 3-mo at 25° C./60% RH | 3-mo at 40° C./75% RH |
|---|---|---|---|
| Cetirizine Dihydrochloride lot# ODT (S9A239 - Opaque PVC/PVdC) | | | |
| Assay (10 mg/tablet) for Stability Performance | 102.9% LC* (10.29 mg/tablet) | 101.4% LC (10.14 mg/tablet) | 101.2% LC (10.12 mg/tablet) |
| Disintegration Time | 5-10 seconds | 5-10 seconds | 10-15 seconds |
| Dissolution: | | | |
| Dissolved in 5 Min | 98% | 99% | 98% |
| Dissolved in 30 min | 100% | 100% | 99% |
| Impurities: | 0.74 | 0.92% | 0.90% |
| Individual Known: | 0.02% | | |
| Impurity A (RRT 1.35) | | 0.15% | 0.13% |
| Impurity F (RRT 0.48) | | <0.005% | ND |
| Impurity G (RRT 1.51) | | 0.27% | 0.36% |
| Individual Unknown: | 0.24% | | |
| RRT 0.52 | | ND | 0.01% |
| RRT 0.61 | | 0.05% | 0.14% |
| RRT 0.72 | | 0.35% | 0.13% |
| RRT 0.79 | | <0.005% | <0.005% |
| RRT 0.87 | | 0.10% | 0.13% |
| Moisture | 1.84% | 2.08% | 3.88% |
| Cetirizine Dihydrochloride ODT (lot# S9A235 - Clear Aclar) | | | |
| Assay (10 mg/tablet) | 102.7% LC (10.27 mg/tablet) | 102.3% LC (10.23 mg/tablet) | 199.3% LC (9.93 mg/tablet) |
| Disintegration Time | 5-10 seconds | 5-10 seconds | 5-10 seconds |
| Impurities: | 0.87% | 0.72% | 1.84% |
| Individual Known: | 0.05% | | |
| Impurity A (RRT 1.35) | | 0.13% | 0.24% |
| Impurity F (RRT 0.48) | | 0.01% | <0.005% |
| 0.13% | | 0.22% | 0.72% |
| 0.01% | 0.27% | | |
| 0.22% | | ND | 0.01% |
| Individual Unknown: | | 0.03% | 0.24% |
| RRT 0.52 | | 0.33% | 0.43% |
| RRT 0.61 | | ND | 0.20% |
| RRT 0.72 | | | |
| RRT 0.87: | | | |
| Moisture | 1.77% | 1.59% | 2.39% |

*LC refers to the label claim of 10 mg for Zyrtec ® and Zyrtec ® Chewable tablets.

I claim:

1. An orally disintegrating composition comprising:
   a. taste-masked microparticles, each comprising:
      i. a core particle comprising a substituted benzhydrylpiperazine or a pharmaceutically acceptable salt, ester, and/or solvate thereof; and
      ii. a taste-masking layer comprising a water-insoluble polymer and a gastrosoluble polymer disposed over the core particle, and,
   b. rapidly dispersing microgranules each comprising:
      i. a disintegrant and
      ii. a sugar alcohol, a saccharide, or a mixture thereof, wherein the ratio of sugar alcohol and/or saccharide to disintegrant is from about 99:1 to about 90:10,
   wherein after administration said disintegrating composition substantially disintegrates in the oral cavity of a patient, wherein said taste-masking layer substantially masks the taste of the substituted benzhydrylpiperazine acceptable salt, ester, and/or solvate thereof, and wherein said orally disintegrating composition releases not less than 75% of said substituted benzhydrylpiperazine or a pharmaceutically acceptable salt, ester, solvate, and/or combination thereof within 15 minutes when dissolution tested using United States Pharmacopeia Apparatus 1 (baskets @ 100 rpm) or Apparatus 2 (paddles @50 rpm) in 900 mL of 0.1N HCl.

2. The orally disintegrating composition of claim 1, wherein in the taste-masked micro particles each further comprise seal-coating layer surrounding said core particle, and disposed beneath said taste-masking layer.

3. The orally disintegrating composition of claim 2, wherein said seal-coating layer comprises hydroxypropylcellulose.

4. The orally disintegrating composition of claim 1, wherein said core particle comprises a substituted benzhydrylpiperazine selected from the group consisting of hydroxyzine, cetirizine, efletirizine, meclizine, buclizine, or a pharmaceutically acceptable salt, ester and/or solvate thereof.

5. The orally disintegrating composition of claim 1, wherein said substituted benzhydrylpiperazine is cetirizine dihydrochloride.

6. The orally disintegrating composition of claim 1, wherein said substituted benzhydrylpiperazine is levocetirizine dihydrochloride.

7. The orally disintegrating composition of claim 1, wherein said core particle is in the form of a drug-layered inert particle, a crystalline material, or a microgranule.

8. The orally disintegrating composition of claim 1, wherein said core particle comprises an inert particle surrounded by a drug coating, and the drug coating comprises:
a. a substituted benzhydrylpiperazine or a pharmaceutically acceptable salt, ester, and/or solvate thereof; and
b. an optional polymeric binder.

9. The orally disintegrating composition of claim 7, wherein said inert particle comprises a sugar sphere, a microcrystalline cellulose sphere, or a silicon dioxide sphere.

10. The orally disintegrating composition of claim 8, wherein the drug coating comprises a substituted benzhydrylpiperazine or a pharmaceutically acceptable salt, ester, and/or solvate thereof and a polymeric binder, and said polymeric binder is selected from the group consisting of polyvinyl pyrrolidone, polyethylene oxide, hydroxypropyl methylcellulose, hydroxypropyl cellulose, modified starch, poly (vinyl acetate-vinylpyrrolidone) and mixtures thereof.

11. The orally disintegrating composition of claim 10, wherein said inert particle comprises a sugar sphere and said polymeric binder comprises polyvinyl pyrrolidone or hydroxypropyl cellulose.

12. The orally disintegrating composition of claim 8, wherein said core particle has an average particle size of not more than about 350 μm.

13. The orally disintegrating composition of claim 8, wherein said drug coating constitutes from about 5% to about 15% of said core particle.

14. The orally disintegrating composition of claim 7, wherein the core particle is in the form of a crystalline material, and said crystalline material has an average particle size of not more than about 250 μm.

15. The orally disintegrating composition of claim 7, wherein the core particle is in the form of a microgranule, and said microgranule comprises a substituted benzhydrylpiperazine and/or a pharmaceutically acceptable salt, ester, or solvate thereof and a polymeric binder.

16. The orally disintegrating composition of claim 8, wherein the drug coating comprises a substituted benzhydrylpiperazine or pharmaceutically acceptable salt, ester, and/or solvate thereof and a polymeric binder, and said polymeric binder is selected from the group consisting of polyvinyl pyrrolidone, hydroxypropyl cellulose, modified starch, poly(vinyl acetate-vinylpyrrolidone), hydroxypropyl methylcellulose, and combinations thereof.

17. The orally disintegrating composition of claim 7, wherein the core particle is in the form of a microgranule, and said microgranule further comprises a filler selected from the group consisting of lactose and microcrystalline cellulose.

18. The orally disintegrating composition of claim 1, wherein said water-insoluble polymer is selected from the group consisting of ethylcellulose, cellulose acetate, cellulose acetate butyrate, methacrylate copolymers, and mixtures thereof.

19. The orally disintegrating composition of claim 18, wherein said water-insoluble polymer is ethylcellulose.

20. The orally disintegrating composition of claim 1, wherein said gastrosoluble polymer is selected from the group consisting of terpolymers of dimethylaminoethyl methacrylate, butyl methacrylate, and methyl methacrylate; maltodextrins, aminoalkyl methacrylate copolymers, polyvinylacetal diethylaminoacetate, and mixtures thereof.

21. The orally disintegrating composition of claim 16, wherein said gastrosoluble polymer is a copolymer of one or more acrylic acid esters and one or more methacrylic acid esters with alkylamino groups.

22. The orally disintegrating composition of claim 1, wherein the ratio of water-insoluble polymer to gastrosoluble polymer ranges from about 95/5 to about 30/70.

23. The orally disintegrating composition of claim 1, wherein said taste-masking layer comprises from about 5% to about 50% by weight of the combined weight of the core particle and taste-masking layer.

24. The orally disintegrating composition of claim 1, wherein said taste-masking layer comprises from about 10% to about 30% by weight of the combined weight of the core particle and taste-masking layer.

25. The orally disintegrating composition of claim 1, wherein said taste-masking layer further comprises a plasticizer.

26. The orally disintegrating composition of claim 25, wherein said plasticizer is selected from the group consisting of triacetin, polyethylene glycol, tributyl citrate, triethyl citrate, acetyl tri-n-butyl citrate, diethyl phthalate, castor oil, dibutyl sebacate, acetylated monoglycerides, and mixtures thereof.

27. The orally disintegrating composition of claim 1, wherein said taste-masking layer further comprises an anti-tacky agent selected from the group consisting of talc and magnesium stearate.

28. The orally disintegrating composition of claim 1, wherein said rapidly dispersing granules have an average particle size of about 300 μm or less.

29. The orally disintegrating composition of claim 1, wherein said disintegrant and said sugar alcohol and/or said saccharide have an average particle size of about 30 μm or less.

30. The orally disintegrating composition of claim 1, wherein said disintegrant is selected from the group consisting of crospovidone, sodium starch glycolate, crosslinked sodium carboxymethylcellulose, low-substituted hydroxypropy cellulose, and mixtures thereof.

31. The orally disintegrating composition of claim 1, wherein said sugar alcohol, saccharide or mixture thereof is selected from the group consisting of mannitol, sorbitol xylitol, and maltitol.

32. The orally disintegrating composition of claim 1, wherein said disintegrant comprises crospovidone and said sugar alcohol, saccharide or mixture thereof comprises mannitol.

33. The orally disintegrating composition of claim 1, further comprising microcrystalline cellulose.

34. The orally disintegrating composition of claim 1, further comprising one ore excipients selected from the group consisting of a flavoring agent, a sweetener, a colorant, and mixtures thereof.

35. The orally disintegrating composition of claim 1, wherein said orally disintegrating composition is substantially free of lubricant.

36. The orally disintegrating composition of claim 1, wherein the ratio of said microparticles to said rapidly dispersing granules ranges from about 1:1 to about 1:10 by weight.

37. The orally disintegrating composition of claim 1, wherein said orally disintegrating composition substantially disintegrates in the oral cavity within about 60 seconds after contact with saliva.

38. The orally disintegrating composition of claim 1, wherein said orally disintegrating composition releases not less than about 75% of said substituted benzhydrylpiperazine or a pharmaceutically acceptable salt, ester, solvate and/or combination thereof within about 30 minutes when tested for dissolution in United States Pharmacopoeia Apparatus 1 (paddles at 100 rpm in 900 mL of simulated gastric fluid or 0.1 N HCl).

39. The orally disintegrating composition of claim 1, wherein said orally disintegrating composition releases not more than about 10% of said substituted benzhydrylpiperazine or a pharmaceutically acceptable salt, ester, solvate, and/or combination thereof within about 5 minutes when dissolution tested in United States Pharmacopeia Apparatus 1 (paddles at 100 rpm in 900 mL of pH 6.8 buffer or simulated saliva fluid).

40. A stabilized tablet comprising the orally disintegrating composition of claim 1.

41. The tablet of claim 40, wherein said tablet has a friability of about 1% or less.

42. The tablet of claim 40, wherein said tablet has a hardness value of at least about 25N.

43. The tablet of claim 40, wherein said tablet retains at least about 90% of its initial potency after storage at 30° C. at 65% RH for at least about 12 months.

44. The tablet of claim 40, wherein said tablet retains at least about 90% of its initial potency after storage at 40° C. and 75% RH for at least about 6 months.

45. The tablet of claim 40, wherein said tablet retains at least about 90% of its initial potency after storage at 25° C. and 60% RH for at least about 3 years.

46. The tablet of claim 40, wherein said tablet has total impurities of less than about 4% after storage at 80° C. and 75% RH for at least about 4 days.

47. The tablet of claim 40, wherein said tablet shows total impurities of less than about 2% after storage at 80° C. and 75% RH for at least about 4 days.

48. The tablet of claim 40, wherein said tablet shows total impurities of less than about 1% after storage at 80° C. and 75% RH for at least about 4 days.

49. A method of treating an allergic or inflammatory disorder comprising administering to a patient in need thereof a pharmaceutical dosage form comprising the composition of claim 1.

50. A method of preparing the orally disintegrating composition of claim 1 comprising:
a. preparing core particles comprising a substituted benzhydrylpiperazine or a pharmaceutically acceptable salt, ester, and/or solvate thereof;
b. layering said core particles with a taste-masking layer comprising a water-insoluble polymer and a gastrosoluble polymer,
wherein said taste-masking layer substantially masks the taste of the substituted benzhydrylpiperazine or a pharmaceutically acceptable salt, ester, and/or solvate thereof.

51. The method of claim 50, wherein said substituted benzhydrylpiperazine is selected from the group consisting of cetirizine, efletirizine, meclizine, and buclizine, or a pharmaceutically acceptable salt, ester, and/or solvate thereof.

52. The method of claim 50, wherein said substituted benzhydrylpiperazine is cetirizine dihydrochloride.

53. The method of claim 50, wherein said water-insoluble polymer is selected from the group consisting of ethylcellulose, cellulose acetate, cellulose acetate butyrate, methacrylate copolymers, and mixtures thereof.

54. The method of claim 50, wherein said water-insoluble polymer is ethylcellulose.

55. The method of claim 50, wherein said gastrosoluble polymer is selected from the group consisting of maltodextrins, aminoalkyl methacrylate copolymers, polyvinylacetate diethaminoacetate, and mixtures thereof.

56. The method of claim 50, wherein said gastrosoluble polymer comprises aminoalkyl methacrylate copolymers.

57. The method of claim 50, wherein said step of preparing said core particles comprises:
i. dissolving or suspending a substituted benzhydrylpiperazine or pharmaceutically acceptable salt, ester, and/or solvate thereof in a solution comprising a polymeric binder; and
ii. layer the solution or suspension of step (i) onto inert particles,
wherein said inert particles comprise sugar spheres, microcrystalline cellulose spheres, or silicon dioxide spheres.

58. The method of claim 57, wherein said layering step (ii) is carried out in fluid-bed coating equipment.

59. The method of claim 57, further comprising layering a seal coat onto said core particles.

60. The method of claim 59, wherein said seal coat comprises hydroxypropylcellulose.

61. The method of claim 50, wherein said step of preparing core particles comprises:
i. granulating a substituted benzhydrylpiperazine or a pharmaceutically acceptable salt, ester, and/or solvate thereof, a diluent, and a polymeric binder to form a granulated mixture;
ii. extruding and spheronizing said granulated mixture.

62. The method of claim 50, wherein said layering step comprises:
i. dissolving said water-insoluble polymer and said gastrosoluble polymer in a solution comprising an organic solvent, water, and a plasticizer;
ii. suspending talc in said solution; and
iii. coating said core particles with the suspension of step (ii).

63. A method for preparing the orally disintegrating composition of claim 1 comprising:
a. coating core particles comprising a substituted benzhydrylpiperazine or a pharmaceutically acceptable salt, ester, and/or solvate thereof with one or more taste-masking layers to form coated microparticles;

b. preparing granules comprising (i) a disintegrant and (ii) a sugar alcohol, a saccharide, or a mixture thereof;

c. mixing said coated microparticles and said granules to form a compressible blend; and d. compressing said compressible blend into tablets.

64. The method of claim 63, wherein said compressing step is carried out using a rotary tablet press.

65. The method of claim 64, wherein said compressible blend is substantially free of lubricant and said rotary table press has externally lubricated punches and dies.

66. A method for preparing the stabilized tablet of claim 40 comprising:

a. coating an inert particle comprising a sugar sphere, a microcrystalline cellulose sphere, or a silicon dioxide sphere, with a drug layer comprising a substituted benzhydrylpiperazine or a pharmaceutically acceptable salt, ester, and/or solvate thereof, then coating with a water-insoluble polymer in combination with a gastrosoluble polymer, thereby forming coated microparticles;

b. preparing granules comprising a disintegrant and a low molecular weight polyol;

c. mixing said coated microparticles and said granules to form a compressible blend; and d. compressing said compressible blend into a tablet.

67. The method of claim 66, wherein said low molecular weight polyol comprises a sugar alcohol.

\* \* \* \* \*